United States Patent

Migachyov

[11] Patent Number: 5,996,585
[45] Date of Patent: Dec. 7, 1999

[54] NONSURGICAL INTRAURETHRAL BLADDER CONTROL DEVICE RETAINER

[75] Inventor: Valery Migachyov, San Antonio, Tex.

[73] Assignee: HK Medical Technologies Incorporated, San Antonio, Tex.

[21] Appl. No.: 08/916,431

[22] Filed: Aug. 21, 1997

[51] Int. Cl.[6] .................................................. A61F 5/48
[52] U.S. Cl. ............................ 128/885; 128/DIG. 25; 600/29
[58] Field of Search .................................. 128/885, 886, 128/DIG. 25; 600/29–31; 604/329, 330

[56] References Cited

U.S. PATENT DOCUMENTS

| | | | |
|---|---|---|---|
| 3,731,670 | 5/1973 | Loe | 128/1 |
| 3,812,841 | 5/1974 | Isaacson | 128/1 |
| 4,553,533 | 11/1985 | Leighton | 128/1 |
| 4,679,546 | 7/1987 | van Waalwijk van Doorn et al. | 128/1 |
| 4,934,999 | 6/1990 | Bader | 600/29 |
| 4,955,858 | 9/1990 | Drews | 604/8 |
| 4,968,294 | 11/1990 | Salama | 600/30 |
| 4,969,474 | 11/1990 | Schwarz | 128/885 |
| 5,007,894 | 4/1991 | Enhorning | 600/29 |
| 5,007,898 | 4/1991 | Rosenbluth et al. | 604/54 |
| 5,012,822 | 5/1991 | Schwarz | 128/885 |
| 5,041,092 | 8/1991 | Barwick | 604/104 |
| 5,078,676 | 1/1992 | Bailly | 600/31 |
| 5,088,980 | 2/1992 | Leighton | 600/30 |
| 5,090,424 | 2/1992 | Simon et al. | 128/885 |
| 5,097,848 | 3/1992 | Schwarz | 128/885 |
| 5,112,306 | 5/1992 | Burton et al. | 604/101 |
| 5,114,398 | 5/1992 | Trick et al. | 600/29 |
| 5,123,428 | 6/1992 | Schwarz | 128/885 |
| 5,140,999 | 8/1992 | Ardito | 128/885 |
| 5,417,226 | 5/1995 | Juma | 128/885 |
| 5,512,032 | 4/1996 | Kulisz et al. | 600/29 |
| 5,624,395 | 4/1997 | Mikhail | 604/93 |
| 5,701,916 | 12/1997 | Kulisz | 128/885 |
| 5,711,314 | 1/1998 | Ardito | 128/885 |

FOREIGN PATENT DOCUMENTS

WO 96/18431  6/1996  WIPO .

Primary Examiner—Michael A. Brown
Attorney, Agent, or Firm—Crompton, Seager & Tufte, LLC

[57] ABSTRACT

A bladder control apparatus retaining device for placement within the urethra of a patient. The device includes a sheath having distal and proximal ends and an internal lumen for receiving a bladder control apparatus. Disposed at opposite ends are first and second retainers. The sheath and retainers are preferably a flexible polymer which can be coated or impregnated with an antibiotic.

5 Claims, 4 Drawing Sheets

NONSURGICAL INTRAURETHRAL BLADDER CONTROL DEVICE RETAINER

FIELD OF THE INVENTION

The present invention relates generally to the field of medical devices; more particularly to intraurethral bladder control devices; still more particularly to intraurethral bladder control devices with retaining means; and, yet more particularly to a sheath for a nonsurgically implanted intraurethral bladder control device.

DESCRIPTION OF THE PRIOR ART

The use of intraurethral bladder control devices, often referred to as artificial sphincters, is widespread in the field of the present invention. The use of intraurethral valving apparatus is generally known in this field of art as can be evidenced by, for example, U.S. Pat. Nos. 4,553,533; 4,679,546; 4,969,474; and 5,123,428.

A specific one of such bladder control devices is fully described in U.S. patent application Ser. No. 08/515,920, filed Aug. 16, 1995, and assigned to the assignee of this invention. That particular bladder control device solved a continuing problem found in the prior art by providing safe and secure retention of the bladder control device in the urethra by providing an improved intraurethral bladder control device with retainer apparatus. A first retainer was mounted to the distal end of the bladder control housing and operated within the bladder to hold the housing within the urethra. A second retainer apparatus was connected to the proximal end of the bladder control device and extended proximately out of the urethra where a portion thereof was put into abutment with the labia.

As used throughout this specification, the term "distal" or "distal end" shall mean the end of a device or internal lumen which is intended to be closest to the bladder, and the term "proximal end" or "proximal" shall mean the end of the device or lumen which is closest to the labia.

The above-described retaining means for an intraurethral bladder control device was found to accomplish its goal of solving the problem of safe and secure retention of the bladder control device in the urethra. However, an additional problem was found by physicians who utilized the bladder control device. This problem comprised the bodily discomfort caused by the intraurethral bladder control device after insertion into the urethra, because of the effects of the metal or other hard surface of the device as felt on the walls of the urethra.

SUMMARY OF THE INVENTION

The apparatus of this invention overcomes the problems of discomfort after placement of a bladder control device into the urethra by providing a sheath comprised of a material more compatible with the body. For example, the sheath of this invention may comprise a flexible cylindrical body having an inner portion adapted to receive a urethral flow control device and to hold the device within the sheath securely. Retaining means are provided at the proximal and distal ends of the sheath to hold it and the bladder control device it contains within a urethra. In various preferred embodiments described below, use may be made of preferred shapes of distal and proximal retainers and various materials compatible with the body may be used for the sheath and the retainers. Certain means described below may also be placed at the ends of the sheath in the internal lumen, defined by the sheath, to prevent excess movement of the bladder control device within the lumen.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which drawings like reference numerals designate like part throughout the figures thereof and wherein.

DETAILED DESCRIPTION OF THE PREFERRED EMBODIMENTS

Figure 1:
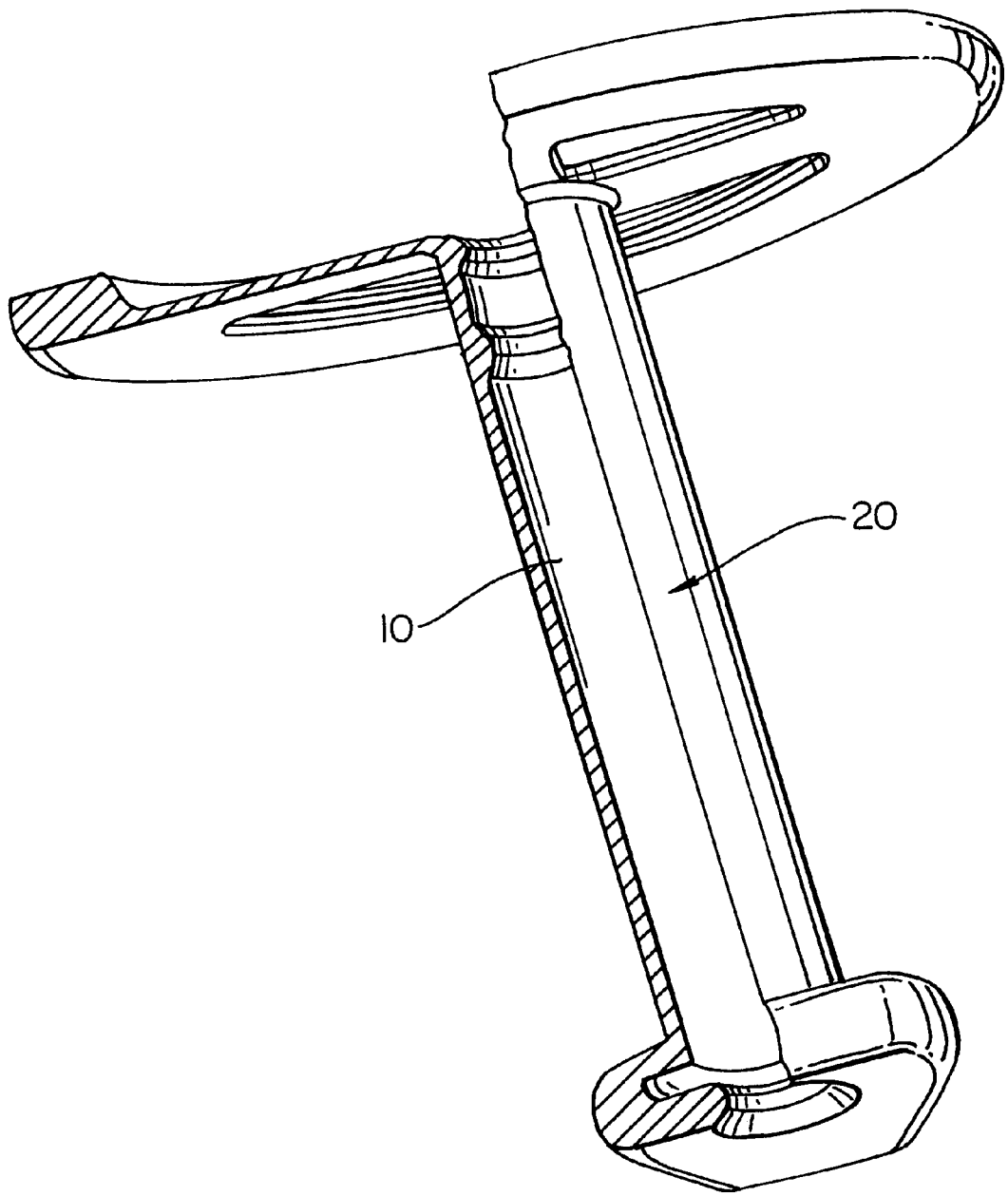
FIG. 1 is a perspective representational view of a prior art intraurethral bladder control apparatus with retaining means at its proximal end and distal ends.

FIG. 1 discloses a perspective view of a representation of a prior art intraurethral bladder control device 10 disposed with a sheath 20 of the present invention. Bladder control device 10 includes a plurality of flow control valves (not shown). Bladder control device 10 is disclosed in detail in U.S. Pat. No. 5,437,604, which issued Aug. 1, 1995 and which is incorporated herein by reference.

Figure 2:
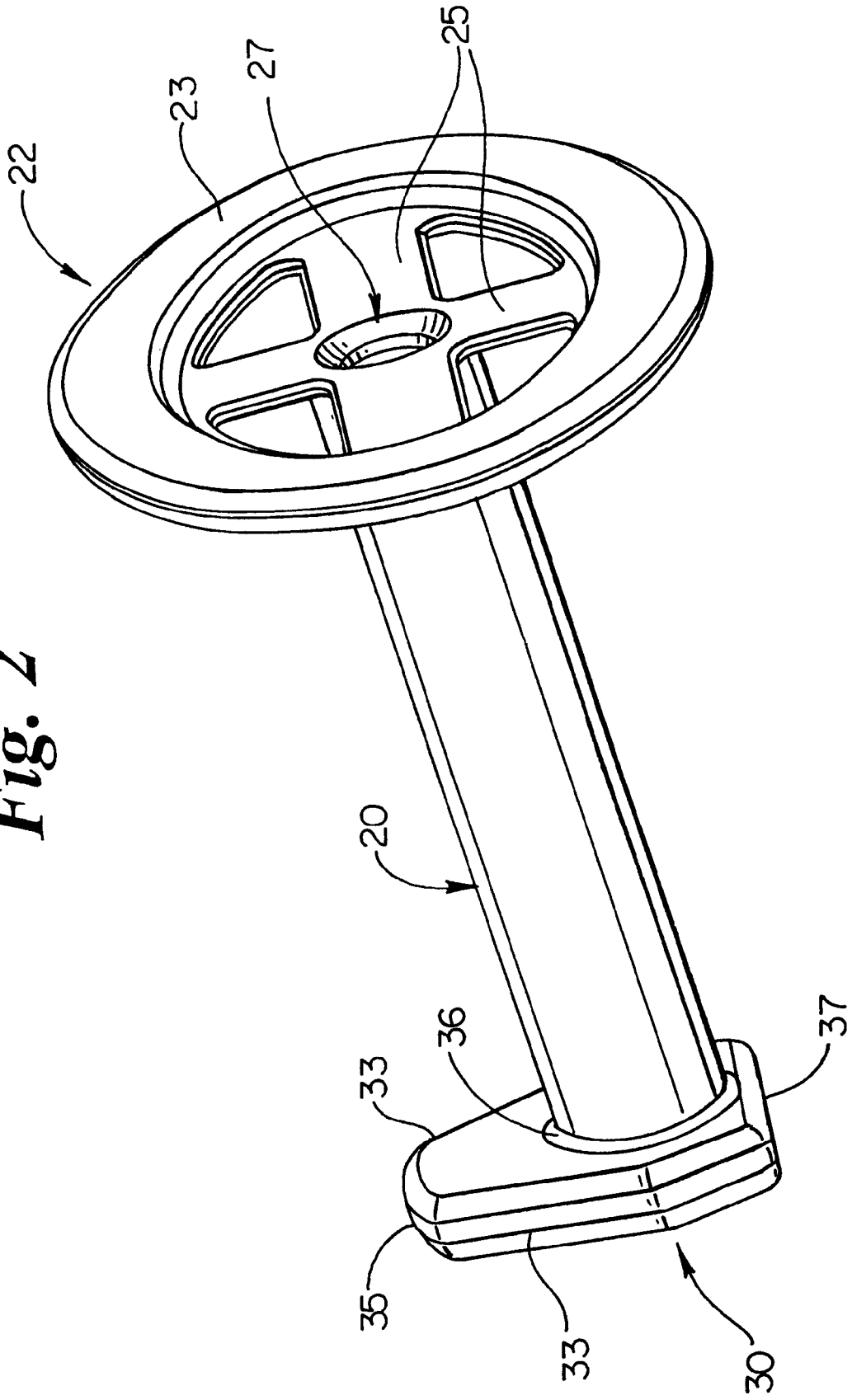
FIG. 2 is a perspective view of the sheathing apparatus of this invention having distal and proximal retaining means.

The apparatus of this invention, as shown in FIG. 2, includes a sheath 20 which is comprised of a flexible body-compatible material such as, by way of example, silicone rubber. By way of design, it is preferred that sheath 20 be of a cylindrical shape having an internal lumen which when unflexed has a diameter slightly smaller than the external diameter of the intraurethral bladder control device the sheath is adapted to receive into its internal lumen. Thus, the sheath will have to be expanded to receive the intraurethral bladder control device and thus the natural contraction process of the flexible material will tend to hold the intraurethral bladder control device in place.

The matter of material used to manufacture the sheath, it is desirable to have the wall of sheath 20 as thin as possible without risking excessive tearing of the material. This use of the thin wall will enable keeping the French size of the ensheathed bladder control device as close to the original French sizes of the intraurethral bladder control device as possible.

In FIG. 2 there is shown an elliptical distal or bladder retaining means 22. Retaining means 22 includes an external, rounded elliptical wheel 23 connected to an attachment means 26 (not shown in FIG. 2 but shown in FIG. 3), by a plurality of spokes or radii 25. A flow aperture 27 is provided through retaining means 22 to allow for the flow of fluid from a bladder into the distal end of the intraurethral bladder control device within sheath 20.

Also shown in FIG. 2 is a proximal retaining means 30, connected to the proximal end of sheath 20 by an attachment means 36, here shown as an attachment ring. Retainer 30 is generally shoe-shaped and includes a toe side 35, a pair of hip-to-hip sides 33, and a dorsal side 37.

Figure 3:
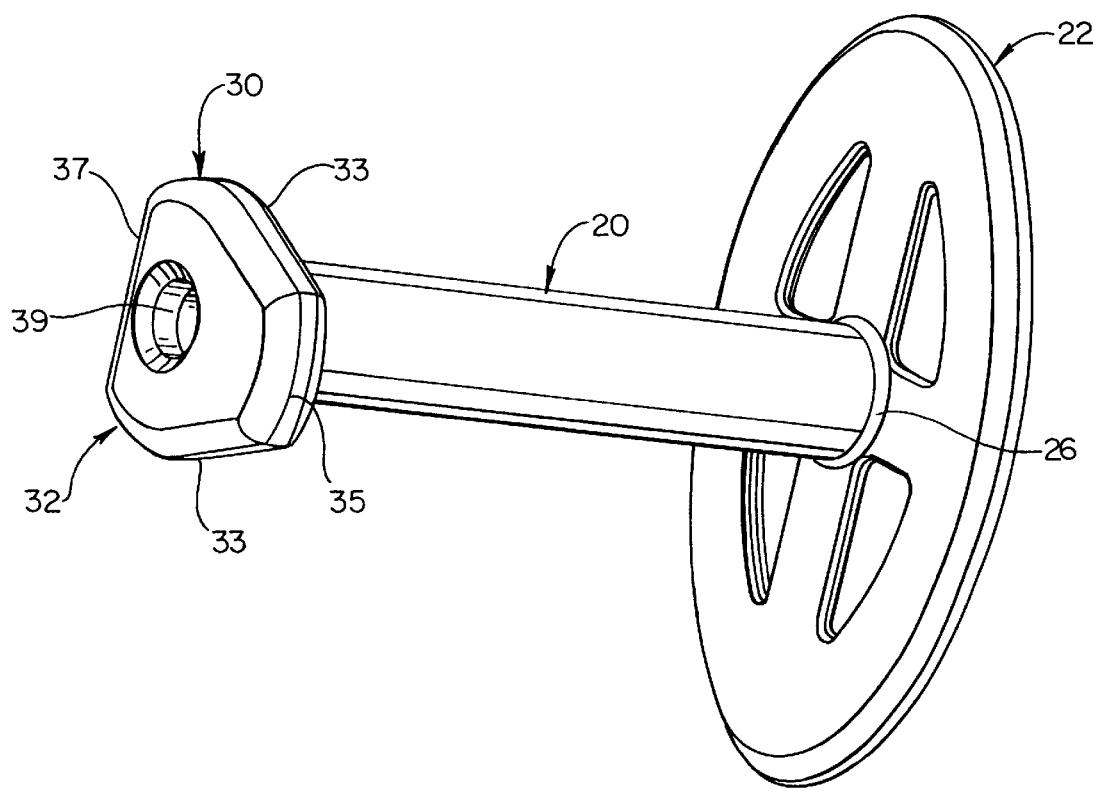
FIG. 3 is another perspective view of the apparatus of FIG. 2.

Referring now to FIG. 3, it can be seen that an attachment means 26 connects retaining means 22 to sheath 20 at its distal end. It can also be seen that retaining means 32 includes an aperture 39 to allow for flow of fluid from the bladder of the patient out through the urethra of the patient, after flowing through the intraurethral bladder control device contained within sheath 20.

Figure 4:
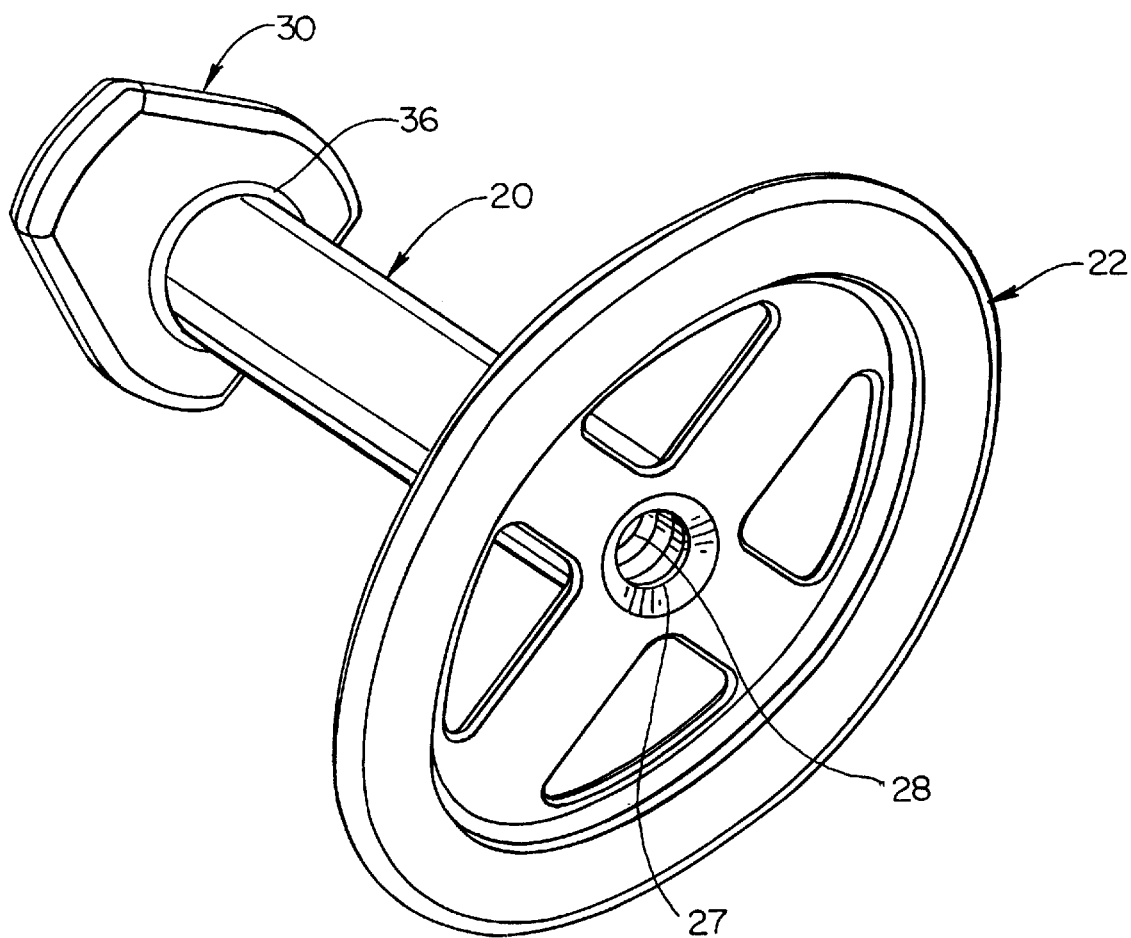
FIG. 4 is yet another perspective view of the apparatus of FIG. 2.

Lastly, referring to FIG. 4, one can see through aperture 27 of retaining means 22 that an internal lumen of sheath 20 has mounted therein a retaining ring 28. The purpose of ring 28 will be described below.

Referring now to FIGS. 1–4, all figures of the drawings, the following discussion of the preferred embodiments of the apparatus of this invention will be fully understood.

As briefly described above, sheath 20 is preferably comprised of an "elastomer" bio-compatible material, such as silicon rubber. In a preferred embodiment, sheath 20 and retainers 22 and 30 are coated with an antimicrobial agent, such as an antimicrobial protein. The antimicrobial agent can also be impregnated into sheath 20. The internal lumen of sheath 20 is designed to have an "at rest" or unflexed diameter which is slightly smaller than the external diameter of the intraurethral bladder control device it is to receive. Thus when a metallic or other hard-surfaced intraurethral bladder control device such as housing 12 of FIG. 1, is placed within the internal lumen of sheath 20, it will be necessary to flex the lumen to insert the intraurethral bladder control device, and the contraction of the flexible material of sheath 20 will then tend to hold the intraurethral bladder control device in place within sheath 20, thus effectively giving a more desirable outer surface for contact with the human body.

Referring to FIG. 1, it is apparent that retainers 14 and 16 will be removed when housing 12 is placed within sheath 20. Therefore, to retain the advantages of retainers 14 and 16, retaining means 22 and 30 are connected to, respectively, the distal and proximal ends of sheath 20.

Retaining means 22 is preferably elliptically shaped having its long axis positioned laterally (hip-to-hip) thus providing a secure retaining means within the bladder of the patient. Preferably, retaining means 22 is an elliptical ring which is connected by spokes or radii 25 to connection or attachment means 26. Ring 23 is also preferably rounded. The advantages of these preferred shapes and constructions are to reduce physical contact area with the bladder walls, to make folding of the upper retainer part physically easier and to make ring 23 a holding structural element. Thus, as ring 23 is positioned in a lateral or hip-to-hip situs of the rounded wheel 23 will allow for an easier fit of retaining means 22 into the asymmetric space of the bladder's floor.

For purposes of insertion, it is desired that retaining means 22 be folded distally around the axis of sheath 20 for ease of sliding the apparatus of this invention into an insertion tube (not shown). It is apparent that the use of spokes such as 25 enable ease of folding of retaining means 22 and also decreases the quantity, weight and overall area of the material to be used. As stated, it is preferred that the material used to manufacture retaining means 22 be the same as that material used to manufacture sheath 20 such as silicon rubber.

Referring now to retaining means 30 which is shown connected by attachment means 36 to the proximal end of sheath 20, it should again be noted that it is preferable to make sheath 30 of a material that is similar to or the same that from which sheath 20 is manufactured. That is, a biocompatible material such as silicon rubber or elastomer. Shoe-shaped retaining means 30 has this preferred shape for multiple reasons. In addition to being sufficiently thick to perform its retaining purpose, means 30 should have its toe end 35, with an extensive shoulder, extending in the ventral direction. Hip-to-hip sides 33 should have narrower shoulders, and dorsal side 37 should have essentially no shoulder. It has been found that this preferred shape and thickness is advantageous for several reasons: To fit properly into the anatomy of the female genitals; thus to prevent the sheath from slipping into or toward the bladder; and, to reduce interference during vaginal intercourse.

Further with regard to the construction of sheath 20, in addition to the advantage offered by having the internal lumen of sheath 20 of a smaller diameter than the external diameter of the bladder control device to be contained within sheath 20, another preferred embodiment provides an internal ring at the distal and proximal ends of sheath 20, such as ring 28 of FIG. 4, which extending rings will provide additional force for the retention of the intraurethral bladder control device within that sheath 20.

It will be recognized that the above-described invention derives its ultimate utility when properly placed within the urethra of a patient. Various prior art methods of dilation of the urethra for placement of a device such as the present invention are known in the prior art. However, it is believed that the most advantageous apparatus for such placement is fully described in copending U.S. patent application Ser. No. 08/515,564 filed Aug. 16, 1995, entitled BLADDER CONTROL INSERTION APPARATUS, and owned and assigned to the assignee of this invention, and hereby incorporated by reference in this disclosure. It is to simplify the use of the insertion apparatus described in the referenced application that retaining means 22 has been given the shape and characteristics defined above so that it may be readily folded distally along sheath 20 for easy slippage into an insertion tube of the type defined in the application hereby incorporated by reference.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A bladder control apparatus retaining device for placement within the urethra of a patient, the improvement comprising:
    (a) sheath means having distal and proximal ends and including an internal lumen for receiving a bladder control apparatus;
    (b) first retainer means connected to the distal end of said sheath means, and operable within the bladder of a patient, for retaining said sheath means within the urethra of the patient;
    (c) second retainer means connected to the proximal end of said sheath means for extending from the urethra for retaining said sheath means within the urethra; and
    (d) wherein said first retainer means includes an elliptical, flexible ring for placement within the patient's bladder, said elliptical ring having a major axis, and spoke means connecting said ring to the distal end of said sheath means.

2. The improvement of claim 1 in which said second retainer means includes a relatively thick, shoe member having a toe end extending in the ventral direction, a pair of laterally-extending sides, and a lead end with minimal extension in the dorsal direction, said shoe-shaped retainer member being shaped and sized to fit the anatomy of the female genitals; and, means connecting said member to the proximal end of said sheath.

3. The improvement of claims 2 in which all said retainer means comprise an elastomer.

4. Holding apparatus for an intraurethral flow control apparatus comprising:
- (a) a generally cylindrical, elastic sheath having an internal lumen for receiving said flow control apparatus;
- (b) a first retainer means connected to a distal end of said sheath for extending into the bladder when said sheath is in the urethra of a patient, for preventing proximal movement of said sheath in the urethra;
- (c) a second retainer means connected to a proximal end of said sheath for extending proximally from the urethra to abut the labia, for preventing distal movement of said sheath in the urethra; and
- (d) wherein said second retainer means includes a trapezoid member shaped for compatible fit with the female genitals adjacent the urethra.

5. The apparatus of claim 4, in which said first retainer means includes an elliptical ring for extension into the bladder, and a plurality of radii connected one end to said ring and at another end to said distal end of said sheath.

* * * * *